(12) United States Patent
Nohara et al.

(10) Patent No.: US 11,472,707 B2
(45) Date of Patent: Oct. 18, 2022

(54) METHOD FOR MANUFACTURING BACTERIUM-PRODUCED CELLULOSE CARBON

(71) Applicant: Nippon Telegraph and Telephone Corporation, Tokyo (JP)

(72) Inventors: Masaya Nohara, Atsugi (JP); Shuhei Sakamoto, Atsugi (JP); Mikayo Iwata, Atsugi (JP); Masahiko Hayashi, Atsugi (JP); Takeshi Komatsu, Atsugi (JP)

(73) Assignee: Nippon Telegraph and Telephone Corporation, Tokyo (JP)

( * ) Notice: Subject to any disclaimer, the term of this patent is extended or adjusted under 35 U.S.C. 154(b) by 0 days.

(21) Appl. No.: 17/046,993

(22) PCT Filed: Apr. 15, 2019

(86) PCT No.: PCT/JP2019/016079
§ 371 (c)(1),
(2) Date: Oct. 12, 2020

(87) PCT Pub. No.: WO2019/203173
PCT Pub. Date: Oct. 24, 2019

(65) Prior Publication Data
US 2021/0039951 A1    Feb. 11, 2021

(30) Foreign Application Priority Data
Apr. 16, 2018 (JP) .............................. JP2018-078279

(51) Int. Cl.
| C12P 1/00 | (2006.01) |
| C01B 32/05 | (2017.01) |
| C12P 19/04 | (2006.01) |
| C12N 1/20 | (2006.01) |
| C12R 1/01 | (2006.01) |

(52) U.S. Cl.
CPC .............. *C01B 32/05* (2017.08); *C12P 19/04* (2013.01); *C12N 1/205* (2021.05); *C12R 2001/01* (2021.05)

(58) Field of Classification Search
None
See application file for complete search history.

(56) References Cited

U.S. PATENT DOCUMENTS

| 10,023,846 B2 * | 7/2018 | Nishie ...................... C12N 7/00 |
| 10,072,250 B2 * | 9/2018 | Sakamoto ................ C12N 7/00 |
| 10,276,876 B2 * | 4/2019 | Kim ..................... H01M 4/9083 |
| 2008/0118970 A1 * | 5/2008 | Konz ....................... C12N 7/00 435/239 |
| 2017/0098827 A1 * | 4/2017 | Kim ........................ C01B 32/15 |
| 2021/0163293 A1 * | 6/2021 | Nohara ................... C01B 32/15 |

FOREIGN PATENT DOCUMENTS

| CN | 106698389 A | 5/2017 |
| WO | 2003/025271 A1 | 3/2003 |
| WO | 2015/109272 A1 | 7/2015 |

OTHER PUBLICATIONS

International Search Report dated Jul. 16, 2019, issued in PCT Application No. PCT/JP2019/016079, filed Apr. 15, 2019.
Jing Kong et al., Chemical Vapor Deposition of Methane for Single-Walled Carbon Nanotubes, Chemical Physics Letters, 292 (1998) pp. 567-574.
Sumio Iijima et al., Single-Shell Carbon Nanotubes of 1-nm Diameter, Nature, vol. 363, Jun. 17, 1993, pp. 603-605.
Koon-Yang Lee et al., Bacterial Cellulose as Source for Activated Nanosized Carbon for Electric Double Layer Capacitors, Journal Material Science, vol. 48, 2013, pp. 367-376.

* cited by examiner

*Primary Examiner* — Hope A Robinson
(74) *Attorney, Agent, or Firm* — Workman Nydegger

(57) ABSTRACT

There is provided a method for manufacturing a bacterium-produced cellulose carbon having a sufficient specific surface area, and a high mechanical strength. The method manufactures a bacterium-produced cellulose carbon by carbonizing cellulose produced by thermally treating, and the method includes a cellulose forming step S1 of forming bacterium-produced cellulose whereby cellulose nanofibers are dispersed using a bacterium; an impregnating step S2 for impregnating the bacterium-produced cellulose with a supercritical fluid; a drying step S3 of vaporizing the supercritical fluid from the bacterium-produced cellulose containing the supercritical fluid and obtaining a dry product; and a carbonizing step S4 of heating and carbonizing the dry product in an atmosphere not causing combustion of the dry product.

13 Claims, 4 Drawing Sheets

(a)

(b)

(a)

(b)

METHOD FOR MANUFACTURING BACTERIUM-PRODUCED CELLULOSE CARBON

CROSS-REFERENCE TO RELATED APPLICATIONS

This Application is a 35 U.S.C. § 371 nationalization of International Application No. PCT/JP2019/016079, filed Apr. 15, 2019, which claims priority to Japanese Application No. 2018-078279, filed Apr. 16, 2018.

TECHNICAL FIELD

The present invention relates to a method for manufacturing a bacterium-produced cellulose carbon.

BACKGROUND ART

A carbon nanofiber is generally in the shape of a fiber with an outer diameter of 5 to 100 nm, and a fiber length 10 or more times the outer diameter. The specific shape results in features such as high electric conductivity and high specific surface area.

Conventionally, as methods for manufacturing a carbon nanofiber, for example, a discharge method, a gas phase growth method, and a laser method are known (e.g., NPL 1 and 2).

CITATION LIST

Non Patent Literature

[NPL 1] S. Iijima et al. "Single-shell carbon nanotubes of 1-nm diameter", Nature, Vol. 363, 17 Jun. 1993.

[NPL 2] J. Kong et al. "Chemical vapor deposition of methane for single-walled carbon nanotubes", Chemical Physics Letters 292, 567-574, 1998.

SUMMARY OF THE INVENTION

Technical Problem

However, mass production is difficult with a conventional manufacturing method. Accordingly, there is room for improvement in terms of cost. Further, generally, bacterium-produced cellulose contains a large amount of water. With a conventional manufacturing method (drying step), the cellulose fibers of bacterium-produced cellulose aggregate due to the surface tension of water in association with evaporation of water. For this reason, it is undesirably not possible to obtain a sufficient specific surface area.

The present invention has been made in view of the problem. It is an object of the present invention to provide a method for manufacturing a bacterium-produced cellulose carbon having a sufficient specific surface area, and having a high mechanical strength.

Means for Solving the Problem

It is summarized that a method for manufacturing a bacterium-produced cellulose carbon in accordance with one aspect of the present invention is a method for manufacturing a bacterium-produced cellulose carbon by carbonizing cellulose produced by bacterium by thermally treating, and includes a cellulose forming step of forming bacterium-produced cellulose that cellulose nanofibers are dispersed using a bacterium; an impregnating step of impregnating the bacterium-produced cellulose with a supercritical fluid; a drying step of vaporizing the supercritical fluid from the bacterium-produced cellulose containing the supercritical fluid and obtaining a dry product; and a carbonizing step of heating and carbonizing the dry product in an atmosphere not causing combustion of the dry product.

Effects of the Invention

In accordance with the present invention, it is possible to provide a method for manufacturing a bacterium-produced cellulose carbon having a sufficient specific surface area and a high mechanical strength.

DESCRIPTION OF EMBODIMENTS

Embodiments of the present invention will be described below by way of the drawings.

First Embodiment

Figure 1:
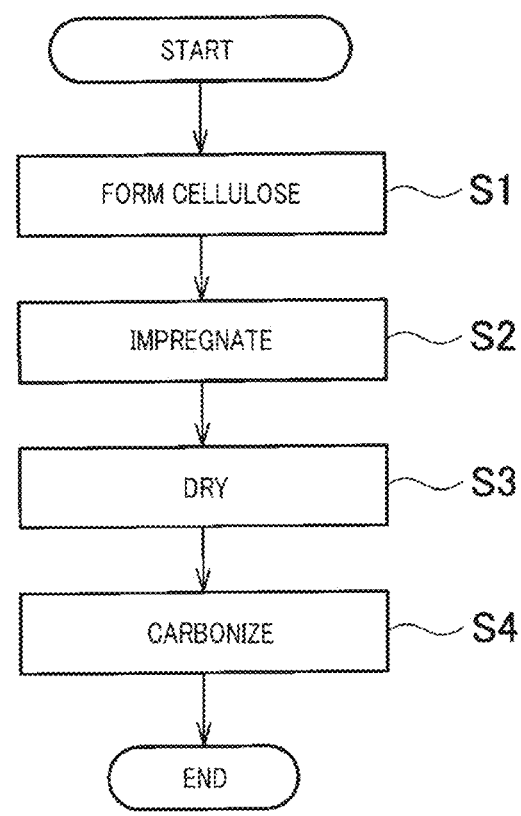
FIG. 1 is a flowchart showing a method for manufacturing a bacterium-produced cellulose carbon in accordance with a first embodiment of the present invention.

FIG. 1 is a flowchart showing a method for manufacturing a bacterium-produced cellulose carbon in accordance with a first embodiment of the present invention. In the description from this point forward, the bacterium-produced cellulose carbon may also be referred to as a carbon material.

A method for manufacturing a bacterium-produced cellulose carbon of the present embodiment includes a cellulose forming step (step S1), an impregnating step (step S2), a drying step (step S3), and a carbonizing step (step S4).

The cellulose forming step forms bacterium-produced cellulose that cellulose nanofibers are dispersed using a bacterium (step S1). The bacterium-produced cellulose formed here is in a gel shape. The substance "in a gel shape" means a substance that has lost the flowability to be put into a solid state due to the three-dimensional network structure of a nano structure in which the disperse medium is a dispersoid. Further, a nanofiber is defined as a fibrous substance with a diameter of from 1 nm to 1 μm, and with a length 10 or more times the diameter.

The gel disperse medium is a water type such as water ($H_2O$), or an organic type such as carboxylic acid, methanol ($CH_3OH$), ethanol ($C_2H_5OH$), propanol ($C_3H_7OH$), n-butanol, isobutanol, n-butyl amine, dodecane, unsaturated fatty acid, ethylene glycol, heptane, hexadecane, isoamyl alcohol, octanol, isopropanol, acetone, or glycerine. Two or more of these may be mixed.

The gel produced by a bacterium includes a fiber of nanometer order as the basic structure. The carbon material obtained by manufacturing a carbon material using the gel has a high specific surface area. Specifically, by using the gel produced by a bacterium (which will be hereinafter referred to as a bacterium-produced gel), it is possible to synthesize a carbon material having a specific surface area of 300 m$^2$/g or more.

The bacterium-produced gel has a structure including fibers tangled in a coil form or a network form, and further has a structure including nanofibers branched based on the growth of a bacterium. For this reason, the carbon material which can be manufactured achieves an excellent elasticity of a strain at the elastic limit of 50% or more.

As bacteria, known ones may be mentioned. For example, acetic acid bacteria such as *Acetobacter xylinum* subsp. *sucrofermentans, Acetobacter xylinum* ATCC23768, *Acetobacter xylinum* ATCC23769, *Acetobacter pasteurianus* ATCC10245, *Acetobacter xylinum* ATCC14851, *Acetobacter xylinum* ATCC11142, and *Acetobacter xylinum* ATCC10821, and those produced by cultivating various mutant strains created by subjecting these to mutation processing based on a known method using NTG (nitrosoguanidine), or the like are desirable.

Then, an impregnating step is carried out. The impregnating step impregnates the bacterium-produced cellulose with a supercritical fluid (step S2). A specific impregnating step is carried out in the following manner. For example, a bacteria-produced gel is accommodated in a container filled with carbon dioxide, hydrofluoro ether, or the like; and the inside of the container is put in a high pressure state to cause the bacterium-produced cellulose to be impregnated with a supercritical fluid.

For the supercritical fluid, known ones can be used. Examples thereof include carbon dioxide, water. methane, ethane, propane, ethylene, propylene, methanol, ethanol, acetone, and fluorine type liquid such as hydrofluoro ether. Two or more of the liquids may be mixed.

The conditions for achieving the supercritical state vary depending on the liquid. For carbon dioxide, for example, a pressure of 7.38 MPa or more may be applied at a temperature of 31° C. or higher. For hydrofluoro ether, a pressure of 2.55 MPa or more may be applied at a temperature of 191° C. or higher.

Supercritical liquid has low surface tension and low viscosity. Further, the diffusion coefficient thereof is large. For this reason, by impregnating a bacterium-produced gel with a supercritical liquid, the supercritical fluid readily penetrates into the gap of the microstructure. Accordingly, the fluid such as water contained in the bacterium-produced gel can be rapidly removed to the outside of the bacterium-produced gel.

Then, the drying step is carried out. The drying step vaporizes a supercritical fluid from bacterium-produced cellulose containing the supercritical fluid, thereby obtaining a dry product (bacterium-produced xerogel) (step S3). A specific drying step is carried out in the following manner. The pressure of the inside of the container accommodating therein the bacterium-produced gel containing the supercritical fluid obtained in the impregnating step is reduced, thereby vaporizing the supercritical fluid.

The conditions for vaporizing the supercritical fluid vary depending on the fluid. The conditions have no particular restriction so long as they are the conditions for vaporizing a disperse medium. For example, for carbon dioxide it may be an ordinary temperature in the case of ordinary pressures. For hydrofluoro ether, a temperature in a range from 50° C. to 200° C. is preferable in the case of ordinary pressures. Further, the evacuation of the inside of the container results in the reduction in the boiling point. This enables vaporization of the supercritical fluid at lower temperatures.

Then, the carbonizing step is carried out. The carbonizing step heats and carbonizes the dry product obtained in the drying step in an atmosphere not causing combustion of the dry product (step S4). A specific carbonizing step burns and carbonizes the dry product, for example, at 500° C. to 2000° C., more preferably 900° C. to 1800° C. in an inert gas atmosphere. Examples of the gas not causing combustion of cellulose include inert gases such as a nitrogen gas and an argon gas. A carbon dioxide or carbon monoxide gas having an activating effect on a carbon material, and capable of expecting high activation is more preferable.

As described up to this point, the method for manufacturing a carbon material in accordance with the present embodiment is a method for manufacturing a bacterium-produced cellulose carbon by carbonizing cellulose produced by bacterium by thermally treating. The method includes a cellulose forming step (step S1) of forming bacterium-produced cellulose that cellulose nanofibers are dispersed using a bacterium; an impregnating step (step S2) of impregnating the bacterium-produced cellulose with a supercritical fluid; a drying step (step S3) of drying the supercritical fluid from the bacterium-produced cellulose containing the supercritical fluid and obtaining a dry product; and a carbonizing step (step S4) of heating and carbonizing the dry product in an atmosphere not causing combustion of the dry product.

This suppresses the aggregation due to the surface tension involved with the evaporation of the disperse medium in the drying step because after the bacterium-produced cellulose is impregnated with the supercritical fluid, the supercritical fluid is vaporized, and the bacterium-produced cellulose is dried for carbonization. As a result, it is possible to readily mass produce a nanofiber carbon having a three-dimensional network structure of a bicontinuous product in which cellulose nanofibers are continuously connected, and having a high specific surface area, being porous, and having a high strength.

Further, with the method for manufacturing a bacterium-produced cellulose carbon in accordance with the present embodiment, it is possible to mass produce naturally occurring bacterium-produced cellulose. Therefore, it is also possible to obtain the effect of largely reducing the cost of the nanofiber carbon. Still further, the effect of being able to readily provide a fibrous carbon is also exerted.

The carbon material manufactured using the bacterium-produced gel as described above can enhances the adhesion with the electrode, pore, living tissue, device connection part, and the like. Further, the carbon material has high electric conductivity, corrosion resistance, and a high specific surface area, and hence is suitable for a battery, a capacitor, a fuel battery, a biofuel battery, a microbial battery, a catalyst, a solar battery, a semiconductor manufacturing process, medical devices, beautification equipment, a filter, a heat-resistant material, a flameproof material, a heat insulating material, a conductive material, an electromagnetic shielding material, an electromagnetic noise absorbent, a heat generator, a microwave heat generator, cone paper, clothes, a carpet, a mirror antifoggant, a sensor, a touch panel, and the like.

For the purpose of checking the effects of the manufacturing method described up to this point, an experiment was performed for comparing the carbon material manufactured based on the manufacturing method of the present embodiment (Experimental example 1), and the carbon material manufactured based on the manufacturing method in which the impregnating step and the drying step of the manufacturing method of the present embodiment are not carried out, in other words, the carbon material was obtained by drying bacterium-produced cellulose containing a large amount of moisture in an ordinary manner (Experimental example 2).

Experimental Example 1

A carbon material of Experimental Example 1 was synthesized in the following manner. The following porosity was calculated by modeling the pore as a cylindrical shape from the pore diameter distribution determined by the mercury porosimetry of the carbon material.

First, using an *Acetobacter xylinum* of acetic acid bacteria-produced bacterium cellulose gel, by a supercritical drying device (manufactured by NTT Advanced Technology Corporation), hydrofluoro ether was subjected to a treatment at 200° C. and 2.6 MPa for 12 hours, resulting in a bacterium-produced xerogel (dry product). After drying by the supercritical drying device, the bacterium-produced xerogel was carbonized by burning at 600° C. in a nitrogen atmosphere for 2 hours. As a result, a carbon material was manufactured.

The resulting carbon material was subjected to the XRD measurement, the SEM observation, the porosity measurement, the tensile test, and the BET specific surface area measurement for the evaluation. The resulting carbon material was confirmed to be a carbon (C, PDF card No. 01-071-4630) monophase by the XRD measurement.

The PDF card No. is the card number of the PDF (Powder Diffraction File) of the data base collected by the ICDD (International Centre for Diffraction Data).

Figure 2:
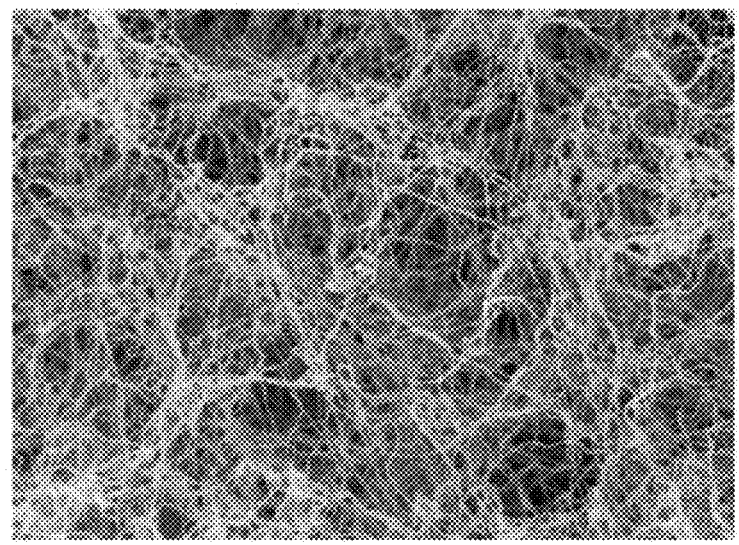
FIG. 2 is an SEM image of a cellulose nanofiber, where (a) of FIG. 2 is an SEM image of a carbon material manufactured by the method shown in FIG. 1, and (b) of FIG. 2 is an SEM image of a carbon material manufactured by a conventional manufacturing method.
Figure 2:
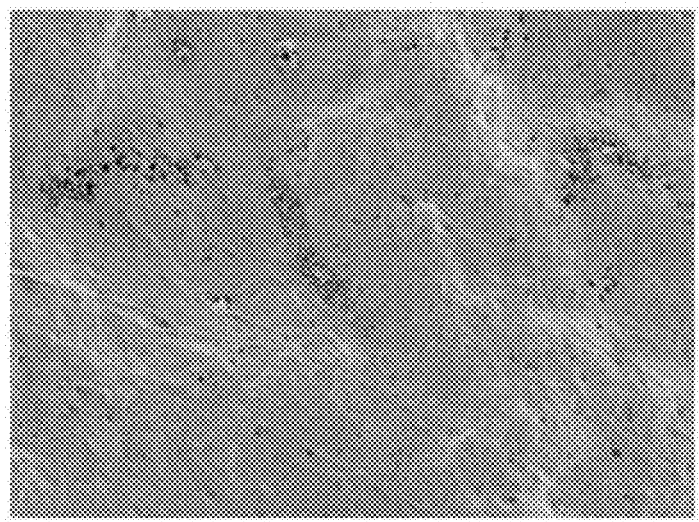

The SEM observation image of the resulting carbon material is shown in (a) of FIG. 2. Further, the evaluation values obtained by performing the measurement are shown in Table 1 (Experimental Example 1 (supercritical drying)).

Experimental Example 2

The bacterium-produced gel used in Experimental Example 1 was placed in a thermostat, and was subjected to a drying treatment at 60° C. for 12 hours. In other words, the manufacturing method of Experiment 2 is a method for manufacturing a carbon material by normally drying bacterium-produced cellulose containing a large amount of water except for the impregnating step (step S2) of impregnating the bacterium-produced cellulose according to the present embodiment with a supercritical fluid.

The resulting carbon material was evaluated by being subjected to the XRD measurement, the SEM observation, the porosity measurement, the tensile test, and the BET specific surface area measurement as in Experimental Example 1. The resulting carbon material was confirmed to be the carbon (C, PDF card No. 01-071-4630) monophase by the XRD measurement.

The SEM observation image of the resulting carbon material is shown in (b) of FIG. 2. Further, the evaluation values obtained by performing the measurement are shown in Table 1 (Experimental Example 2 (ordinary drying)).

FIG. 2 is the SEM observation image of each carbon material obtained in Experimental Examples 1 and 2. (a) of FIG. 2 is the SEM observation image of the carbon material obtained in Experimental Example 1. (b) of FIG. 2 is the SEM observation image of the carbon material obtained in Experimental Example 2. In either case, the magnification is 10,000 times.

As shown in (a) of FIG. 2, the carbon material obtained by the manufacturing method in accordance with the present embodiment was found to be a bicontinuous product including nanofibers, each having a diameter of 30 nm and is continuously connected to one another. On the other hand, the carbon material obtained by normally drying moisture-containing bacterium-produced cellulose was found to be a carbon material having no pores, and densely aggregated.

TABLE 1

| | Specific surface area | Porosity | Tensile strength |
|---|---|---|---|
| Experimental Example 1 (supercritical drying) | 450 m$^2$/g | 75% or more | Confirmed to be resistant to a tensile strength of 130 MPa |
| Experimental Example 2 (ordinary drying) | 1 m$^2$/g | 10% or less | Confirmed to be broken at a tensile strength of 1 MPa or less |

As shown in Table 1, the carbon material manufactured by the manufacturing method in accordance with the present embodiment can more suppress the aggregation due to the surface tension of water involved with the evaporation of the disperse medium than the carbon material manufactured with a conventional drying step of performing ordinary drying. As a result, it could be confirmed that a carbon material having excellent performances of having a high specific surface area, and having elasticity could be provided.

Second Embodiment

Figure 3:
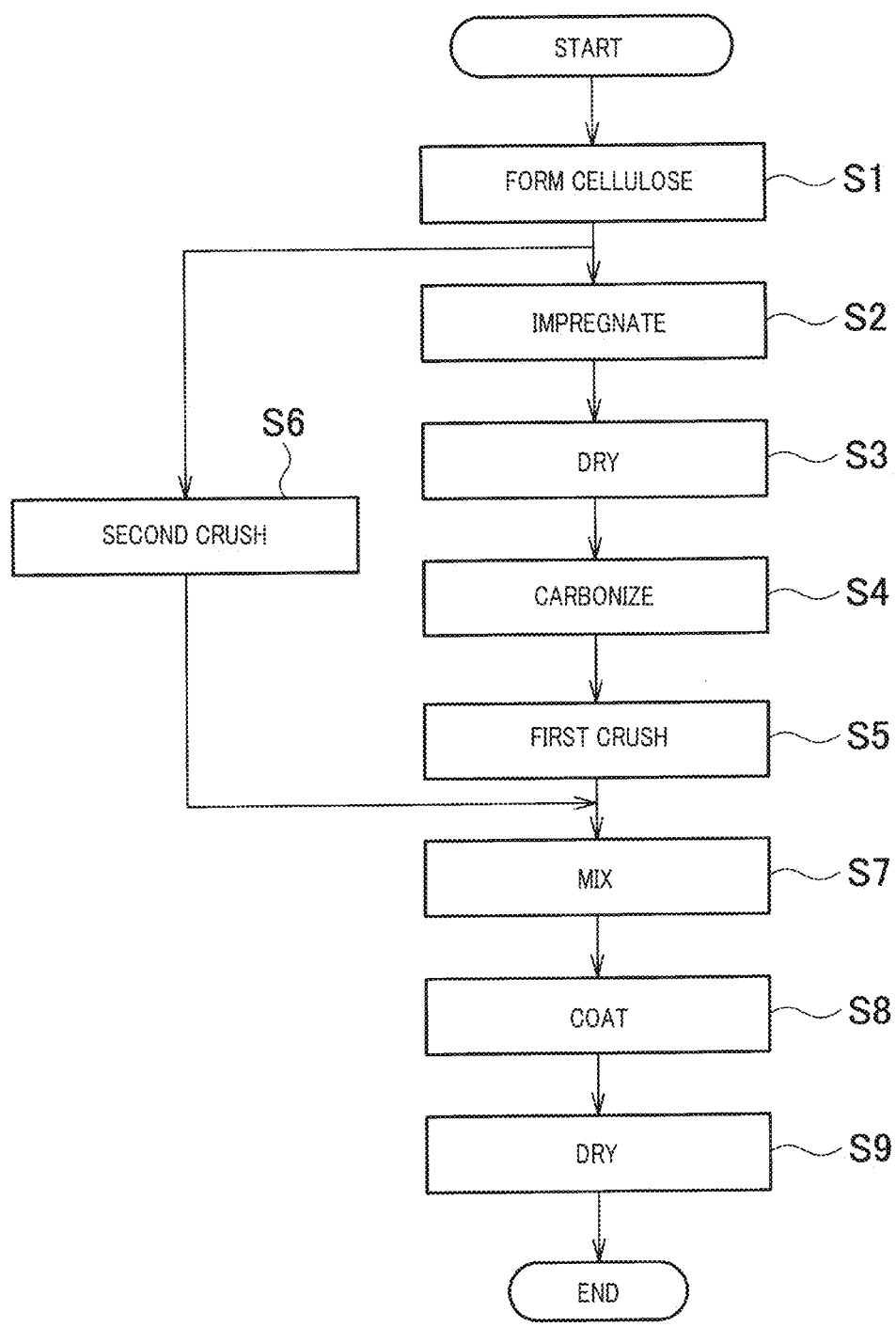
FIG. 3 is a flowchart showing a method for manufacturing a bacterium-produced cellulose carbon in accordance with a second embodiment of the present invention.

FIG. 3 is a flowchart showing a method for manufacturing a bacterium-produced cellulose carbon in accordance with a second embodiment of the present invention. The manufacturing method shown in FIG. 3 is a method for manufacturing a sheet-shaped carbon material, and includes a first crushing step (step S5), a second crushing step (step S6), a mixing step (step S7), a coating step (step S8), and a drying step (step S9) relative to the manufacturing method in the first embodiment.

The first crushing step crushes the dry product that has been carbonized in the carbonizing step (step S4) (step S5). The first crushing step sets the bacterium-produced gel and carbon material into a form of a powder or a slurry using, for example, a mixer, a homogenizer, an ultrasonic homogenizer, a high-speed rotary shearing type stirrer, a colloid mill, a roll mill, a high-pressure spray type disperser, a rotary ball mill, a vibrating ball mill, a planetary ball mill, an attritor or the like. In this case, each of the bacterium-produced gel and the carbon material has a secondary particle diameter of, preferably 100 nm to 5 mm, and more preferably 1 μm to 1 mm. This is because when crushing is performed until the secondary particle diameter becomes 100 nm or less, the bicontinuous structure due to nanofibers is broken, making it difficult to obtain sufficient binding capacity and conductive path, resulting in an increase in electric resistance. Further, when the secondary particle diameter is 5 mm or more, the bacterium-produced gel functioning as a binding agent is not sufficiently dispersed, making it difficult to keep the sheet shape.

Further, the carbon material has a high porosity, and a low density. For this reason, when the carbon material is crushed alone, the powders of the bacterium-produced carbonized cellulose fly during crushing or after crushing, and is difficult to be handled. For this reason, crushing is preferably performed after impregnating the carbon material with a solvent. The solvent used herein has no particular restriction, and is, for example, water type such as water ($H_2O$) or, organic type such as carboxylic acid, methanol ($CH_3OH$), ethanol ($C_2H_5OH$), propanol ($C_3H_7OH$), n-butanol, isobutanol, n-butyl amine, dodecane, unsaturated fatty acid, ethylene glycol, heptane, hexadecane, isoamyl alcohol, octanol, isopropanol, acetone, or glycerine. Two or more of these may be mixed.

The second crushing step crushes the bacterium-produced cellulose carbon formed in the cellulose forming step (step S6). It is also possible to simultaneously crush the bacterium-produced gel and carbon material. Such situation is preferable because the mixing step can be omitted.

The mixing step mixes materials crushed in the first crushing step and the second crushing step, respectively (step S7). The mixture is in a slurry shape.

The coating step forms the mixture in a slurry shape into a given shape (step S8).

The drying step removes a liquid from the mixture formed (coated) into a given shape in the coating step (step S9). When the slurry-shaped mixture (mixed slurry) is dried, a thermostat, a vacuum dryer, an infrared ray heating dryer, a hot-air dryer, or a suction dryer may be used. Further, by performing suction filtration using an aspirator or the like, the slurry-shaped mixture can be dried rapidly.

The mixed slurry obtained by the manufacturing method of the present embodiment described above may be dried, and formed into a sheet shape, followed by processing into a desirable shape. For example, the resulting sheet-shaped carbon material may be stamped, and cut out into a desirable shape by a blade, a laser cutter, or the like.

By forming the mixed slurry into a given shape, and then, drying, the sheet-shaped carbon material can be processed into a desirable shape. Coating can reduce a material cost of chips and the like occurring during cutting processing, and can provide a carbon material in a given shape according to a user's preference. Further, coating can enhance the strength of the carbon material.

Further, the mixed slurry obtained by the manufacturing method of the present embodiment can be formed into a prescribed shape by being poured into a desirable die. For example, by forming a filter paper into a cone shape, and subjecting the mixed slurry to the suction filtration by using an aspirator, a carbon material in a cone shape can be obtained.

The manufacturing method of the present embodiment is not required to include all the steps. For example, the carbon material subjected to the steps up to the first crushing step, thereby having been put into a crushed state may be used. The term "be used" means "be distributed in that state". Similarly, the carbon material may be subjected to the steps up to the mixing step, and may be distributed in a mixed slurry state.

In other words, the manufacturing method of the present embodiment includes the first crushing step (step S5) of crushing the dry product carbonized in the carbonizing step in the method for manufacturing a bacterium-produced cellulose carbon (FIG. 1) in accordance with the first embodiment. As a result, the carbon material in a crushed state can be distributed.

Further, the manufacturing method of the present embodiment includes a second crushing step (step S6) of crushing the bacterium-produced cellulose formed in the cellulose forming step (step S1), and a mixing step (step S7) of mixing the materials crushed in the first crushing step and the second crushing step, respectively, in the method for manufacturing a bacterium-produced cellulose carbon including the first crushing step (step S5). As a result, the carbon material in a mixed slurry state can be distributed.

Further, the manufacturing method of the present embodiment includes a drying step (step S9) of removing a liquid from the mixture obtained by mixing in the mixing step (step S7). As a result, the carbon material mixed in a crushed state can be distributed.

For the purpose of confirming the effects of the manufacturing method described above, an experiment was performed for comparing the sheet-shaped carbon material (Experimental Example 3) manufactured based on the manufacturing method of the present embodiment and the sheet-shaped carbon material (Experimental Example 4) manufactured based on a conventional manufacturing method.

Experimental Example 3

The carbon material manufactured in Experimental Example 1 was impregnated with water, and then, was crushed with stirring for 12 hours by a homoenergy (manufactured by SMT Co., Ltd.). Accordingly, a slurry including the carbon material dispersed therein was manufactured. Then, the slurry and the bacterium-produced gel (the weight ratio of carbon material and the bacterium-produced gel is 1:1) were stirred for 12 hours to be crushed and mixed.

Then, using an aspirator (manufactured by Shibata Scientific Technology Ltd.), suction filtration was performed, thereby releasing the carbon material from filter paper. Then, the released carbon material was placed in a thermostat, and was subjected to a drying treatment at 60° C. for 12 hours.

The resulting carbon material was evaluated by being subjected to the XRD measurement, the SEM observation, the porosity measurement, the tensile test, and the BET specific surface area measurement as in the Experimental Examples 1 and 2. The resulting carbon material was confirmed to be a mixture of carbon (C, PDF card No. 01-071-4630) and cellulose (Cellulose, PDF card No. 00-003-0226) from the XRD measurement.

Figure 4:
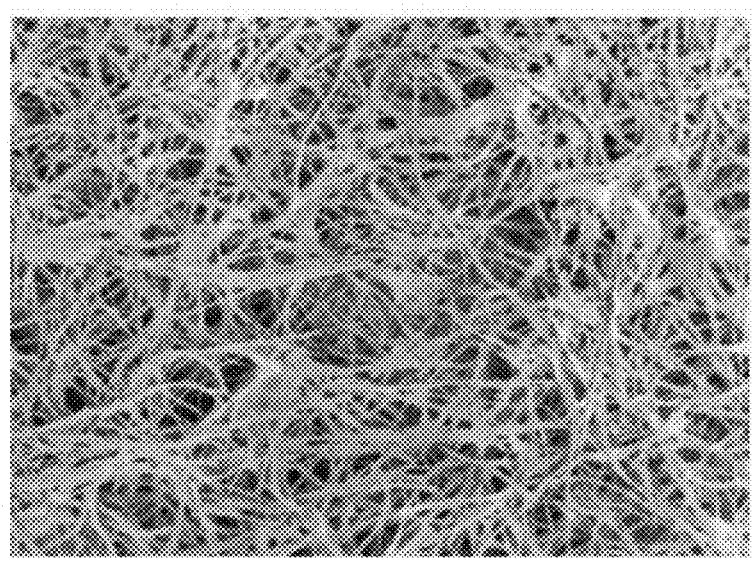
FIG. 4 is an SEM image of a cellulose nanofiber formed in a sheet shape, where (a) in FIG. 4 is an SEM image of a carbon material manufactured by the manufacturing method shown in FIG. 3, and (b) in FIG. 4 is an SEM image of a carbon material manufactured by a conventional manufacturing method (drying step).
Figure 4:
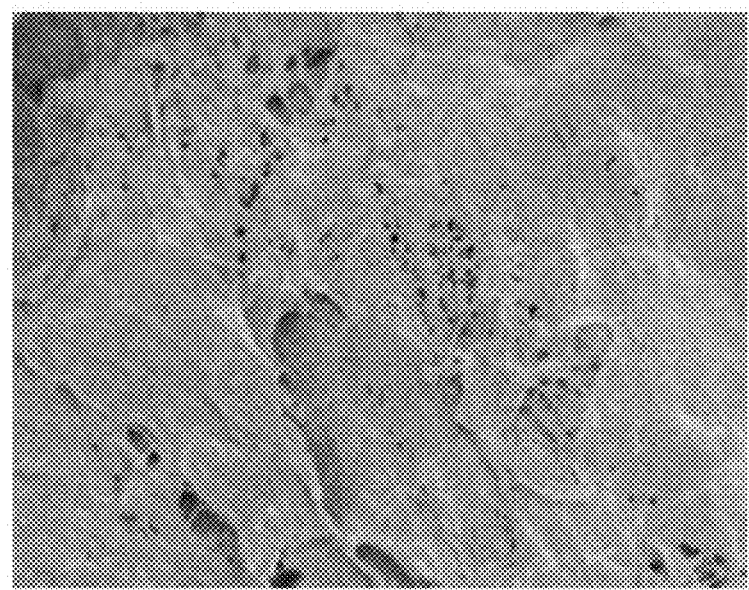

The SEM observation image of the resulting carbon material is shown in (a) of FIG. 4. Further, the evaluation values obtained by performing the measurement are shown in Table 2 (Experimental Example 3 (supercritical drying)).

Experimental Example 4

The carbon material manufactured in Experimental Example 2 (ordinary drying) was impregnated with water, and then, was crushed with stirring for 12 hours by a homoenergy (manufactured by SMT Co., Ltd.), thereby manufacturing a slurry including the carbon material dispersed therein. Then, the slurry and the bacterium-produced gel (the weight ratio of carbon material and the bacterium-produced gel 1:1) were stirred for 12 hours to be crushed and mixed.

Then, using an aspirator (manufactured by Shibata Scientific Technology Ltd.), suction filtration was performed, thereby releasing the carbon material from filter paper. Then, the released carbon material was placed in a thermostat, and was subjected to a drying treatment at 60° C. for 12 hours.

The resulting carbon material was evaluated by being subjected to the XRD measurement, the SEM observation, the porosity measurement, the tensile test, and the BET specific surface area measurement as in the Experimental Example 3. The resulting carbon material was confirmed to be a mixture of carbon (C, PDF card No. 01-071-4630) and cellulose (Cellulose, PDF card No. 00-003-0226) from the XRD measurement.

The SEM observation image of the resulting carbon material is shown in (b) of FIG. 4. Further, the evaluation values obtained by performing the measurement are shown in Table 2 (Experimental Example 4 (ordinary drying)).

FIG. 4 is an SEM observation image of each carbon material obtained in Experimental Examples 3 and 4. (a) of FIG. 4 is an SEM observation image of the carbon material obtained in Experimental Example 3. (b) of FIG. 4 is an SEM observation image of the carbon material obtained in Experimental Example 4. In either case, the magnification is 10,000 times.

As shown in (a) of FIG. 4, the carbon material obtained based on the manufacturing method in accordance with the present embodiment was found to be a bicontinuous product including nanofibers each having a diameter of 30 nm being continuously connected with one another. On the other hand, the carbon material obtained by normally drying moisture-containing bacterium-produced cellulose was found to be a carbon material having no pores, and densely aggregated.

TABLE 2

| | Specific surface area | Porosity | Tensile strength |
|---|---|---|---|
| Experimental Example 3 (supercritical drying) | 450 m$^2$/g | 75% or more | Found to be resistant to a tensile strength of 130 MPa |
| Experimental Example 4 (ordinary drying) | 5 m$^2$/g | 10% or less | — |

As shown in Table 1, the carbon material manufactured based on the manufacturing method in accordance with the present embodiment can more suppress the aggregation than a carbon material in a conventional drying step of performing ordinary drying. As a result, it could be confirmed that a carbon material having excellent performances of having a high specific surface area and having high porosity could be provided.

As has been described above, in accordance with the present embodiments 1 and 2, the method includes an impregnating step of impregnating bacterium-produced cellulose with a supercritical fluid, a drying step of vaporizing the supercritical fluid from the bacterium-produced cellulose containing the supercritical fluid and obtaining a dry product, and a carbonizing step of heating and carbonizing the dry product in an atmosphere not causing combustion of the dry product. With the manufacturing method, the bacterium-produced cellulose is carbonized by being subjected to the heat treatment. For this reason, it is possible to manufacture a carbon material having excellent specific surface area, mechanical strength, and porosity. Further, it is possible to readily obtain a fibrous carbon, which can largely reduce the cost of a nanofiber carbon.

For the carbon material manufactured by the manufacturing method of the present embodiment, naturally occurring cellulose can also be used, resulting in a very low environmental load. Such a carbon material is readily disposable in daily life, and hence can be effectively used in various situations including a compact device, a sensor terminal, medical devices, a battery, beautification equipment, a fuel battery, a biofuel battery, a microbial battery, a capacitor, a catalyst, a solar battery, a semiconductor manufacturing process, a filter, a heat-resistant material, a flameproof material, a heat insulating material, a conductive material, an electromagnetic shielding material, an electromagnetic noise absorbent, a heat generator, a microwave heat generator, cone paper, clothes, a carpet, a mirror antifoggant, a sensor, a touch panel, and the like.

The present invention is not limited to these embodiments, and may be modified within the scope of the gist thereof.

REFERENCE SIGNS LIST

S1 Cellulose forming step
S2 Impregnating step
S3 Drying step
S4 Carbonizing step
S5 First crushing step
S6 Second crushing step
S7 Mixing step
S8 Coating step
S9 Drying step

The invention claimed is:

1. A method for manufacturing a cellulose carbon from a starting cellulose material, the method comprising:
   providing a starting cellulose material, wherein the starting cellulose material is produced by acetic acid bacteria and wherein nanofibers of the starting cellulose material are dispersed;
   impregnating the starting cellulose material with a supercritical fluid to obtain an impregnated cellulose material, wherein the supercritical fluid comprises carbon dioxide, water, methane, ethane, propane, ethylene, propylene, methanol, ethanol, acetone, fluorine-based compounds, hydrofluoro ether, or combinations thereof, and wherein the supercritical fluid is in a supercritical state;
   vaporizing the supercritical fluid from the impregnated cellulose material to obtain a dry product; and
   carbonizing the dry product in an inert atmosphere, not causing combustion of the dry product, to obtain the cellulose carbon.

2. The method of claim 1, further comprising: crushing the dry product.

3. The method of claim 2, further comprising: crushing the starting cellulose material prior to impregnating the starting cellulose material; and mixing the crushed dry product and the crushed starting cellulose material.

4. The method of claim 3, further comprising: removing a liquid from a mixture obtained by mixing the crushed dry product and the crushed starting cellulose material.

5. The method of claim 1, wherein the cellulose nanofibers of the starting cellulose material have a diameter of 1 nm to 1 μm and a length of 10 or more times the diameter.

6. The method of claim 1, wherein the starting cellulose material is provided in a gel disperse medium prior to impregnation with supercritical fluid, wherein the gel disperse medium comprises one or more of water (H2O), carboxylic acid, methanol (CH3OH), ethanol (C2H5OH), propanol (C3H7OH), n-butanol, isobutanol, n-butyl amine, dodecane, unsaturated fatty acid, ethylene glycol, heptane, hexadecane, isoamyl alcohol, octanol, isopropanol, acetone, or glycerine.

7. The method of claim 1, wherein the cellulose carbon has a specific surface area of 300 m$^2$/g or more.

8. The method of claim 1, wherein the starting cellulose material is generated from *Acetobacter* bacteria.

9. The method of claim 1, wherein the starting cellulose material is generated from *Acetobacter xylinum* subsp. *sucrofermentans, Acetobacter xylinum* ATCC23768, *Acetobacter xylinum* ATCC23769, *Acetobacter pasteurianus* ATCC10245, *Acetobacter xylinum* ATCC14851, *Acetobacter xylinum* ATCC11142, or *Acetobacter xylinum* ATCC10821.

10. The method of claim 1, wherein vaporizing the supercritical fluid comprises reducing the pressure in a container in which the impregnated cellulose material is placed.

11. The method of claim 1, wherein carbonizing the dry product comprises heating to a temperature of 500° C. to 2,000° C.

12. The method of claim 1, wherein carbonizing the dry product comprises heating to a temperature of 900° C. to 1,800° C.

13. The method of claim 1, wherein the inert atmosphere comprises nitrogen, argon, carbon dioxide, carbon monoxide, or combination thereof.

* * * * *